(12) United States Patent
Garrison (10) Patent No.: US 10,966,780 B2
(45) Date of Patent: Apr. 6, 2021

(54) ELECTROSURGICAL INSTRUMENT HAVING A COATED ELECTRODE

(75) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 986 days.

(21) Appl. No.: 13/448,577

(22) Filed: Apr. 17, 2012

(65) Prior Publication Data

US 2013/0274736 A1 Oct. 17, 2013

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00107* (2013.01); *A61B 2018/00136* (2013.01); *A61B 2018/00148* (2013.01); *A61B 2018/1452* (2013.01)

(58) Field of Classification Search
CPC ......... A61B 18/00; A61B 18/08; A61B 18/14; A61B 18/18; A61B 5/00; A61B 18/1445; A61B 2018/00107; A61B 2018/00148; A61B 2018/0063; A61B 2018/1452; A61B 2018/00136; A61N 1/00; A61N 1/02; A61N 1/04; A61N 1/05; A61N 1/06; A61N 1/08; A61N 1/18; A61N 1/40; A61N 5/00
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | Decarolis |
| D343,453 S | 1/1994 | Noda |
| D348,930 S | 7/1994 | Olson |
| 5,330,471 A | 7/1994 | Eggers |
| D349,341 S | 8/1994 | Lichtman et al. |
| D354,564 S | 1/1995 | Medema |
| 5,391,166 A | 2/1995 | Eggers |
| D358,887 S | 5/1995 | Feinberg |
| D384,413 S | 9/1997 | Zlock et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael W Kahelin
*Assistant Examiner* — Elizabeth K So (57) ABSTRACT

An instrument and related method includes at least one substrate, and conductive layer, and a coating disposed on the conductive layer. The conductive layer is at partially disposed on the at least one substrate. The coating is disposed on the conductive layer and includes first and second materials. The first material and second materials are different from each other.

18 Claims, 4 Drawing Sheets

(56) References Cited

U.S. PATENT DOCUMENTS

| | | | |
|---|---|---|---|
| 5,713,895 A * | 2/1998 | Lontine | A61B 18/1402 606/41 |
| 5,766,170 A | 6/1998 | Eggers | |
| 5,769,849 A | 6/1998 | Eggers | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| 6,174,309 B1 * | 1/2001 | Wrublewski et al. | 606/45 |
| 6,251,108 B1 * | 6/2001 | Irion | A61B 18/149 600/374 |
| 6,283,961 B1 | 9/2001 | Underwood et al. | |
| D449,886 S | 10/2001 | Tetzlaff et al. | |
| 6,298,550 B1 | 10/2001 | Kirwan, Jr. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,398,782 B1 * | 6/2002 | Pecor | A61B 17/0057 606/46 |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| 6,784,405 B2 | 8/2004 | Flugstad et al. | |
| D496,997 S | 10/2004 | Dycus et al. | |
| D499,181 S | 11/2004 | Dycus et al. | |
| D502,994 S | 3/2005 | Blake III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| 7,150,097 B2 | 12/2006 | Sremcich et al. | |
| D535,027 S | 1/2007 | James et al. | |
| 7,179,255 B2 | 2/2007 | Lettice et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,318,823 B2 | 1/2008 | Sharps et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,553,686 B2 | 6/2009 | George et al. | |
| 7,708,735 B2 | 5/2010 | Chapman et al. | |
| 7,722,607 B2 | 5/2010 | Dumbauld et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,771,425 B2 | 8/2010 | Dycus et al. | |
| 7,776,036 B2 | 8/2010 | Schechter et al. | |
| 7,789,878 B2 | 9/2010 | Dumbauld et al. | |
| 7,799,026 B2 | 9/2010 | Schechter et al. | |
| 7,811,283 B2 | 10/2010 | Moses et al. | |
| D627,462 S | 11/2010 | Kingsley | |
| D628,289 S | 11/2010 | Romero | |
| D628,290 S | 11/2010 | Romero | |
| 7,828,798 B2 | 11/2010 | Buysse et al. | |
| 7,846,161 B2 | 12/2010 | Dumbauld et al. | |
| 7,857,812 B2 | 12/2010 | Dycus et al. | |
| D630,324 S | 1/2011 | Reschke | |
| 7,877,852 B2 | 2/2011 | Unger et al. | |
| 7,877,853 B2 | 2/2011 | Unger et al. | |
| 7,879,035 B2 | 2/2011 | Garrison et al. | |
| 7,887,536 B2 | 2/2011 | Johnson et al. | |
| 7,896,878 B2 | 3/2011 | Johnson et al. | |
| 7,909,823 B2 | 3/2011 | Moses et al. | |
| 7,922,953 B2 | 4/2011 | Guerra | |
| 7,931,649 B2 | 4/2011 | Couture et al. | |
| 7,935,052 B2 | 5/2011 | Dumbauld | |
| 7,947,041 B2 | 5/2011 | Tetzlaff et al. | |
| 7,949,407 B2 | 5/2011 | Kaplan et al. | |
| 7,951,150 B2 | 5/2011 | Johnson et al. | |
| 7,955,331 B2 | 6/2011 | Truckai et al. | |
| 7,963,965 B2 | 6/2011 | Buysse et al. | |
| 7,967,839 B2 | 6/2011 | Flock et al. | |
| 8,016,827 B2 | 9/2011 | Chojin | |
| D649,249 S | 11/2011 | Guerra | |
| D649,643 S | 11/2011 | Allen, IV et al. | |
| 8,070,748 B2 | 12/2011 | Hixson et al. | |
| 2001/0003124 A1 * | 6/2001 | Zolotnitsky | C08K 5/0016 524/401 |
| 2002/0087151 A1 * | 7/2002 | Mody | A61B 18/1492 606/15 |
| 2003/0109864 A1 * | 6/2003 | Greep | A61B 18/14 606/41 |
| 2004/0122423 A1 | 6/2004 | Dycus et al. | |
| 2004/0210282 A1 | 10/2004 | Flock et al. | |
| 2005/0033278 A1 | 2/2005 | McClurken et al. | |
| 2009/0112200 A1 | 4/2009 | Eggers | |
| 2009/0123521 A1 * | 5/2009 | Weber | A61L 31/082 424/426 |
| 2010/0204697 A1 | 8/2010 | Dumbauld et al. | |
| 2011/0077648 A1 | 3/2011 | Lee et al. | |
| 2012/0273256 A1 * | 11/2012 | Chu | G06F 3/044 174/250 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026 179 | 12/2005 |
| DE | 20 2007 009 165 | 10/2007 |
| DE | 20 2007 009 317 | 10/2007 |
| DE | 20 2007 016 233 | 3/2008 |
| DE | 19738457 | 1/2009 |
| DE | 10 2008 018 406 | 7/2009 |
| EP | 0 518 230 A1 | 5/1992 |
| EP | 1159926 | 12/2001 |
| EP | 1946715 A1 | 7/2008 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |

(56) References Cited

FOREIGN PATENT DOCUMENTS

| | | |
|---|---|---|
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2004-532676 A | 10/2004 |
| JP | 2005-523380 A | 8/2005 |
| JP | 2007-098139 A | 4/2007 |
| JP | 2011-125195 | 6/2011 |
| SU | 401367 | 11/1974 |
| WO | WO 94/08524 | 4/1994 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | 03/055449 A1 | 7/2003 |
| WO | WO 05/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 20, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/948,081, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,781, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.

(56) References Cited

OTHER PUBLICATIONS

Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of Hpb Surger, Washington University School of Medicine, St. Louis MO, Presented at Ahpba, Feb. 2001.
Sayfan et al. "Sutureless Closed Hemorrhoidectomy: A New Technique" Annals of Surgery vol. 234 No.1 Jul. 2001; pp. 21-24.
Levy et al., "Update on Hysterectomy—New Technologies and Techniques".
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" Anz Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics Figo World Congress 2000, Washington, D.C.
McLellan et al. "Vessel Sealing for Hemostasis During Gynecologic Surgery" Int'l Federation of Gynecology and Obstetrics FIGO World Congress 2000, Washington, D.C.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.

(56) References Cited

OTHER PUBLICATIONS

Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2069.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT HAVING A COATED ELECTRODE

BACKGROUND

Technical Field

The present disclosure relates to an electrosurgical instrument for treating tissue. More particularly, the present disclosure is related to an electrosurgical instrument having a coated electrode.

Background of Related Art

Electrosurgery involves the application of electricity and/or electromagnetic energy to cut, dissect, ablate, coagulate, seal, or otherwise treat biological tissue during a surgical procedure. Additionally, certain electrosurgical modes invoke the application of electrosurgical energy through a compressed vessel secured between two electrodes to seal the vessel without significant cutting during the sealing process. Electrosurgical cutting, on the other hand, includes applying an electrical spark to tissue in order to produce a cutting or dividing effect. Blending includes the function of cutting combined with the production of a hemostasis effect.

Generally, electrosurgery utilizes an electrosurgical generator, an active electrode and a return electrode. The electrosurgical generator generates an electromagnetic wave (commonly referred to as "electrosurgical energy"), typically above 100 kilohertz to avoid muscle and/or nerve stimulation, between the active and return electrodes when applied to tissue. During electrosurgery, electrosurgical energy is conducted through the patient's tissue disposed between the two electrodes. The electrosurgical energy is returned to the electrosurgical source via a return electrode pad positioned under a patient (e.g., in a monopolar system configuration) or a smaller return electrode positionable in bodily contact with or immediately adjacent to the surgical site (e.g., in a bipolar system configuration). The current causes the tissue to heat up as the electrosurgical energy overcomes the tissue's impedance.

As mentioned above, vessel sealing invokes the application of electrosurgical energy thorough a compressed vessel secured between two electrodes to seal the vessel without significant cutting during the sealing process. The tissue undergoes changes by the applied electrosurgical energy including tissue in direct contact with the electrodes. The tissue in contact with the electrodes sometimes sticks to the electrodes and so-called "eschar" can build up on the electrodes. The eschar must be cleaned or sticking may worsen. Eschar increases the impedance between the electrode and the tissue being treated thus reducing the efficiency of the electrosurgical energy transfer. Also, overall tissue impedance is typically monitored during sealing and the build up of eschar can contribute to higher impedance measurements resulting in increased and/or inconsistent sealing time. Thus, it is desirable to provide electrosurgical electrodes having non-stick surfaces.

SUMMARY

The present disclosure provides for electrodes having a coating may be fully or partially electrically-insulative, fully or partially electrically-conductive, non-stick, gap-forming, and combinations thereof. According to one aspect of the present disclosure, an electrosurgical instrument is provided. The instrument includes a substrate; a conductive layer disposed on the substrate; and a coating layer disposed on the conductive layer. The coating layer includes a first layer comprising a first material, the first layer disposed at least partially over the conductive layer, the first layer including a plurality of surface features and a plurality of spaces therebetween; and a second layer comprising a second material, the second layer disposed at least partially over the first layer to cover at least a portion of the plurality of spaces, wherein the first and second materials are different from each other.

In other aspects of the disclosure, the electrosurgical instrument may be a monopolar instrument, a bipolar instrument, or combinations thereof.

In further aspects of the disclosure, the first and second materials may be porous.

According to another aspect of the disclosure, the coating may fully cover the conductive layer. The first and second materials may be a ceramic, a metal, a polymer, and combinations thereof. The polymer may be polyethylene terephthalate, polytetrafluoroethylene, tetrafluoroethylene, poly(p-xylylene) and combinations thereof. The ceramic may be alumina, zirconia, silica, porcelain, and combinations thereof. The metal may be iron, steel, stainless steel, copper, zinc, aluminum, brass, bronze, nickel, magnesium, titanium, and combinations thereof.

In additional aspects, plurality of surface features are arranged in a two dimensional matrix separated by a first distance in a first direction and a second distance in a second direction. The first and second distances may be the same or different. One or more of the plurality of surface features may at least partially extends through the second layer.

According to another aspect of the disclosure, a method for coating an electrode is disclosed. The method includes applying a first material to a conductive layer to form a first layer disposed at least partially over the conductive layer, the first layer including a plurality of surface features and a plurality of spaces therebetween; and applying a second material to at least one of the conductive layer or the first layer to form a second layer disposed at least partially over the first layer to cover at least a portion of the plurality of spaces, wherein the first and second materials are different from each other.

The method may further include pretreating the conducting layer, wherein the pretreatment is selected from the group consisting of applying a primer to the conductive layer, sandblasting the conductive layer, chemically etching the conductive layer, and combinations thereof.

In further aspects, the first material and the second material is applied to the conductive layer by a process selected from the group consisting of flame spraying, sputtering, spraying, dipping, vapor deposition, ionic deposition, atomic layer deposition, thin film layer deposition, and combinations thereof.

In additional aspects, the first material is a ceramic and the second material is a polymer, and combinations thereof. The polymer may be polyethylene terephthalate, polytetrafluoroethylene, tetrafluoroethylene, poly(p-xylylene) and combinations thereof. The ceramic may be alumina, zirconia, silica, porcelain, and combinations thereof.

In further aspects, the plurality of surface features may be arranged in a two dimensional matrix separated by a first distance in a first direction and a second distance in a second direction and one or more of the plurality of surface features at least partially extends through the second layer.

BRIEF DESCRIPTION OF THE DRAWINGS

Various embodiments are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides an electrosurgical instrument including an electrode having a substrate, a conductive layer, and a coating. The conductive layer is at least partially disposed on the substrate. The coating is disposed on the electrode and includes first and second materials, wherein the first material is different from the second material. The first material and/or the second material may be porous, and may be intermittently disposed on the electrode. The first material may fully or partially cover the electrode.

Suitable electrosurgical instruments according to the present disclosure include any electrosurgical instruments having electrodes for applying radio frequency energy to tissue, including, but not limited to, monopolar instruments, bipolar instruments, ablation probes, return electrode pads, and combinations thereof. To avoid unnecessary disclosure of the various electrosurgical instruments only a bipolar instrument 100 and corresponding electrodes are described in further detail below. The disclosure relating to the electrodes of the bipolar instrument 100 may be applied to form other electrosurgical electrodes.

Figure 1A:
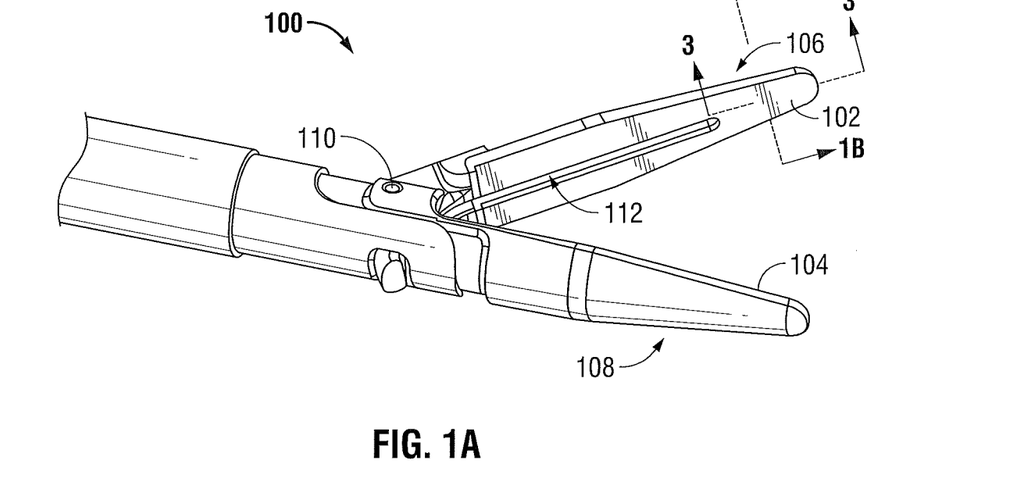
FIG. 1A shows a perspective-view of an electrosurgical instrument having coated electrodes in accordance with an embodiment of the present disclosure.

Referring to the drawings, FIG. 1A is a perspective view of the bipolar instrument 100 having coated electrodes 102 and 104 in accordance with the present disclosure. The electrosurgical instrument 100 seals vessels using electrosurgical energy and includes a movable jaw member 106 and a fixed jaw member 108. The movable jaw member 106 is movable relative to the fixed jaw member 108 about a pivot 110 to grasp tissue between the movable jaw member 106 and the fixed jaw member 108. The movable jaw member 106 supports a first coated electrode 102, and the fixed jaw member 108 supports a second coated electrode 104. Alternatively, only one of the electrodes 102 and 104 may be coated to achieve desired properties. The movable jaw member 106 also defines a channel 112 configured to allow reciprocation of a cutting device (not shown), such as a blade or cutting electrode. The fixed jaw member 108 may also include an opposing cutting channel not viewable from the perspective shown in FIG. 1A. In embodiments, both of the jaw members 106 and 108 may be movable relative to each other. In further embodiments, the instrument 100 may be an open-type forceps.

During an electrosurgical procedure, a blood vessel or other tissue (not shown) is placed between the jaw members 106, 108 while the movable jaw member 106 is in an "open" position (as shown in FIG. 1A), that is, the movable jaw member 106 is spaced apart from the fixed jaw member 108. The surgeon actuates one or more suitable mechanical linkages (not shown) causing the movable jaw member 106 to pivot about the pivot pin 110 towards the fixed jaw member 108, thereby grasping the vessel. The surgeon thereafter activates an electrosurgical generator (not shown) causing electrosurgical energy to flow between coated electrodes 102 and 104 through the grasped vessel. The tissue of the vessel heats up as the electrosurgical energy overcomes impedance of the tissue in the vessel, thereby sealing (e.g., stopping blood flow therethrough) or otherwise treating the vessel.

The electrodes 102 and 104 are coated completely or selectively with two or more materials having different properties, including, but not limited to, an electrical property, such as conductivity or dielectric strength, a thermal property, flexibility, color, a tissue adhesion property, a thickness, and combinations thereof.

Figure 1B:
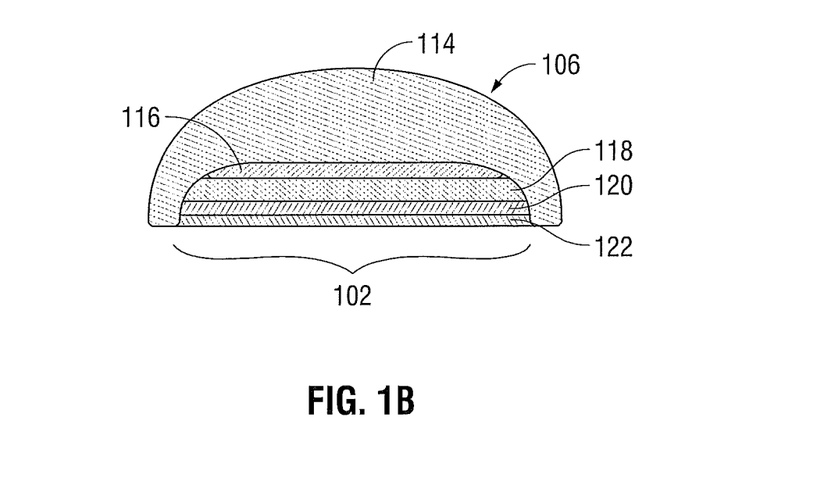
FIG. 1B shows a cross-sectional view along line 1B-1B of the electrosurgical instrument of FIG. 1A in accordance with an embodiment of the present disclosure.

Referring to FIG. 1B, a cross-sectional view along line 1B-1B of the electrosurgical instrument 100 of FIG. 1A is shown. In particular, FIG. 1B shows a cross-sectional view of the movable jaw member 106. To avoid unnecessary disclosure only the electrode 102 is described. The first coated electrode 102 is secured to a base 114 of the movable jaw member 106 via a substrate 116. The substrate 116 may be formed from any suitable material for securing the first coated electrode 102 to the support structure 114, including, but not limited to, various adhesives, which may be reactive, non-reactive, solvent-based, epoxy, thermoplastic, light-curing, heat-curing, and combination thereof. Additionally or alternatively, a fastener (not shown) may be used to secure the electrode 102 to the support structure 114, including, but not limited to, a clip, a screw, a bolt, and the like. In further embodiments, the base 114 may be formed from any suitable insulative thermoplastic material allowing the base 114 to be overmolded to secure the substrate to the base 114. The electrode 102 also includes a conductive layer 118, a first material layer 120, and a second material layer 122. Alternatively, if base 114 is conductive, layers 120 and 122 may be applied directly to base 114. Thus, layers 116 and 118 may be omitted. As discussed above, the material layers 120 and 122 may have various dielectric properties and may be used to form capacitive and/or non-capacitive electrodes.

The first material 120 may be formed as a porous or intermittent coating (see FIGS. 2A-2B and 3A-3C) from any suitable material, including, but not limited to, a ceramic, a metal, a metallic alloy, a polymer, such as thermoplastics, and the like. The first material 120 may be first applied to the electrode 106 to coat at least a portion of the surface of the conductive layer 118. In embodiments, the first material 120 may be applied to coat the entire surface of the conductive layer 118. After the first material 120 is applied, the second material 122 may be applied over the first material 120. The second material 122 may be applied to only a portion of the surface of the first material 120 or the entire surface thereof. In embodiments, the second material 122 may be applied only to the areas that were untreated by the first material 120. The second material 122 may have different properties from the first material 120, such as different electrical, thermal insulation properties, molecular barrier properties, flexibility, color, chemical properties, and the like.

Prior to application of the first material 120, the conductive layer 118 may be chemically or mechanically treated. The conductive layer 118 may be primed, grit and/or sand blasted, chemically etched, and combinations thereof, or otherwise treated to facilitate the adhesion of the first material 120 and/or the second material 122. The first material 120 and the second material 122 may be applied by various methods such as by flame spraying, sputtering, spraying, dipping, vapor deposition, ionic deposition, atomic layer deposition, thin film layer deposition, and combinations thereof. These methods of applying the first material 120 and/or the second material 122 may be controlled for porosity, masking patterns, droplet size, etc.

The first material 120 and/or the second material 122 may be a ceramic, such as alumina, zirconia, silica, porcelain, and combinations thereof, a metal or a metal alloy, such as iron, steel, stainless steel, copper, zinc, aluminum, brass, bronze, nickel, magnesium, titanium, and combinations thereof, a polymer, including, but not limited to, polyethylene terephthalate (PETG), polytetrafluoroethylene, fluoropolymers, such as tetrafluoroethylene sold under a trademark TEFLON® by DuPont of Wilmington, Del., polyp-xylylene) sold under a trademark PARYLENE® and PARYLENE C® by DuPont of Wilmington, Del. In embodiments, the first material 120 may be a ceramic, including but not limited to, such as alumina, zirconia, silica, porcelain, and combinations thereof and the second material 122 may be a flexible polymeric coating formed from any suitable polymer, including but not limited to, polyethylene terephthalate (PETG), polytetrafluoroethylene, fluoropolymers, such as tetrafluoroethylene sold under a trademark TEFLON® by DuPont of Wilmington, Del., poly(p-xylylene) sold under a trademark PARYLENE® and PARYLENE C® by DuPont of Wilmington, Del. The first material 120 may have a dielectric constant of from about 2.9 to about 2,500, in embodiments from about 3.5 to about 1200. The second material 122 may have a dielectric constant from about 1.0 to about 35, in embodiments from about 1.7 to about 25. In further embodiments, the second material 122 may have a dielectric constant from about 0.14% to about 700% of the dielectric constant of the first material 120. The first material 120 may be present in an amount of from about 5% to about 95% by volume of the second material 122, in embodiments of from about 30% to about 90% by volume of the second material 122.

Figure 2A:
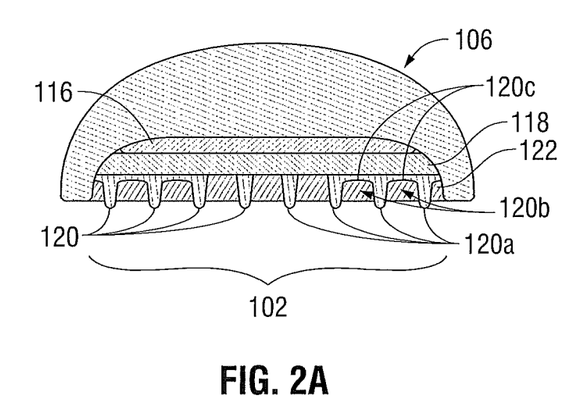
FIGS. 2A-2B show alternative cross-sectional views along line 1B-1B of additional embodiments of the electrosurgical instrument of FIG. 1A in accordance with the present disclosure.
Figure 2B:
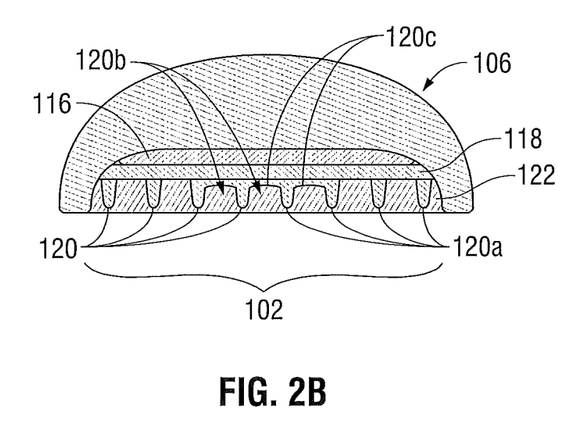

FIGS. 2A-2B show several cross-sectional views along line 1B-1B of the electrosurgical instrument 100 of FIGS. 1A-1B in accordance with the present disclosure. In FIG. 2A, the movable jaw member 106 includes the first material 120 disposed on the conductive layer 118. The first material 120 is applied as a coating using the materials and techniques described above. The first material 120 is applied to form a plurality of surface features 120a and a plurality of spaces 120b (e.g. pores and valleys) disposed therebetween. The surface features 120a may have any suitable shape, including but not limited to, conical, polygonal (e.g., rectangular, hexagonal, star-shaped, etc.), frustoconical, and combinations thereof.

Figure 3A:
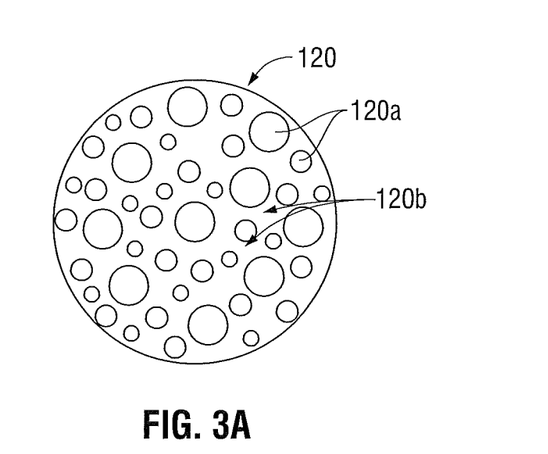
FIGS. 3A-3C show patterns of a material deposited on an electrode to form a coating in accordance with the embodiments of the present disclosure.
Figure 3B:
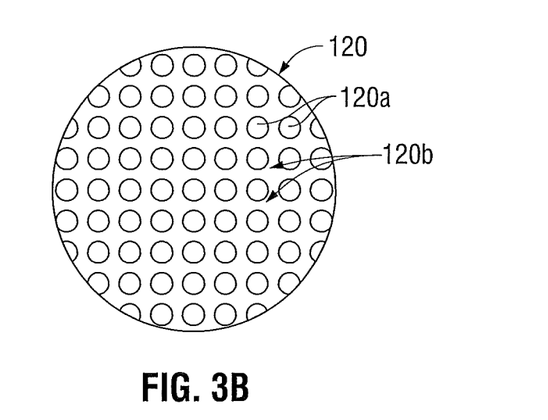
Figure 3C:
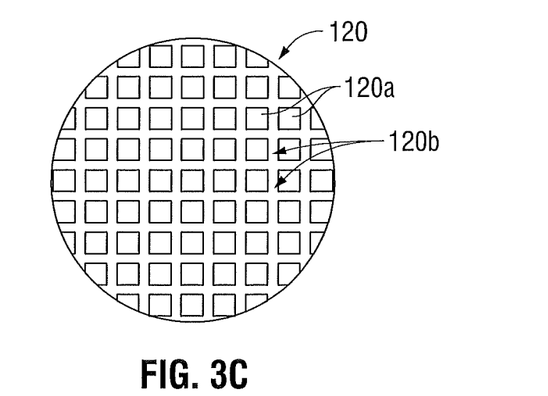

With respect to FIGS. 3A-3C several patterns of the deposited first material 120 are shown along the line 3-3 of FIG. 1A. FIG. 3A shows a pattern of applying the first material 120 to the electrode in a random manner to provide for random location and size of the surface features 120a having a circular shape. FIG. 3B shows another pattern that includes uniformly-sized and positioned surface features 120a having a circular shape arranged in a two dimensional matrix. FIG. 3C shows another pattern of applying a material in another uniform pattern of square shapes including a series of regular rows and columns arranged in a two dimensional matrix. In embodiments, the distance between each surface feature 120a may be the same between any neighboring surface features 120a. In further embodiments, the distance between the surface features 120a may be a first distance in a first direction (e.g., between the rows) and a second distance, different from the first distance in a second direction (e.g., between the columns). The shape, size, and spacing of the surface features 120a may be modified to achieve a desired energy density of the electrode 102.

After application of the first material 120, the second material 122 is applied to fill in the intermittent spaces 122b. The second material 122 is also applied as a coating using the materials and techniques described above. The second material 122 may be applied such that the surface features 120a are exposed as shown in FIG. 2A. In further embodiments, the second material 122 may be applied such that the surface features 120a are wholly covered as shown in FIG. 2B. In embodiments, the surface features 120a may include the first material 120 disposed in a layer 120c therebetween. In further embodiments, the surface features 120a may be disposed directly on the conductive layer 118 with only the second material 122 therebetween.

The layer 120c may be either randomly or uniformly deposited along certain areas of the conductive layer 118. In embodiments, the layer 120c is uniformly deposited may be disposed between the surface features 120a along the periphery of the conductive layer 118 as shown in FIG. 2A or along the center of the conductive layer 118 as shown in FIG. 2B.

Figure 4:
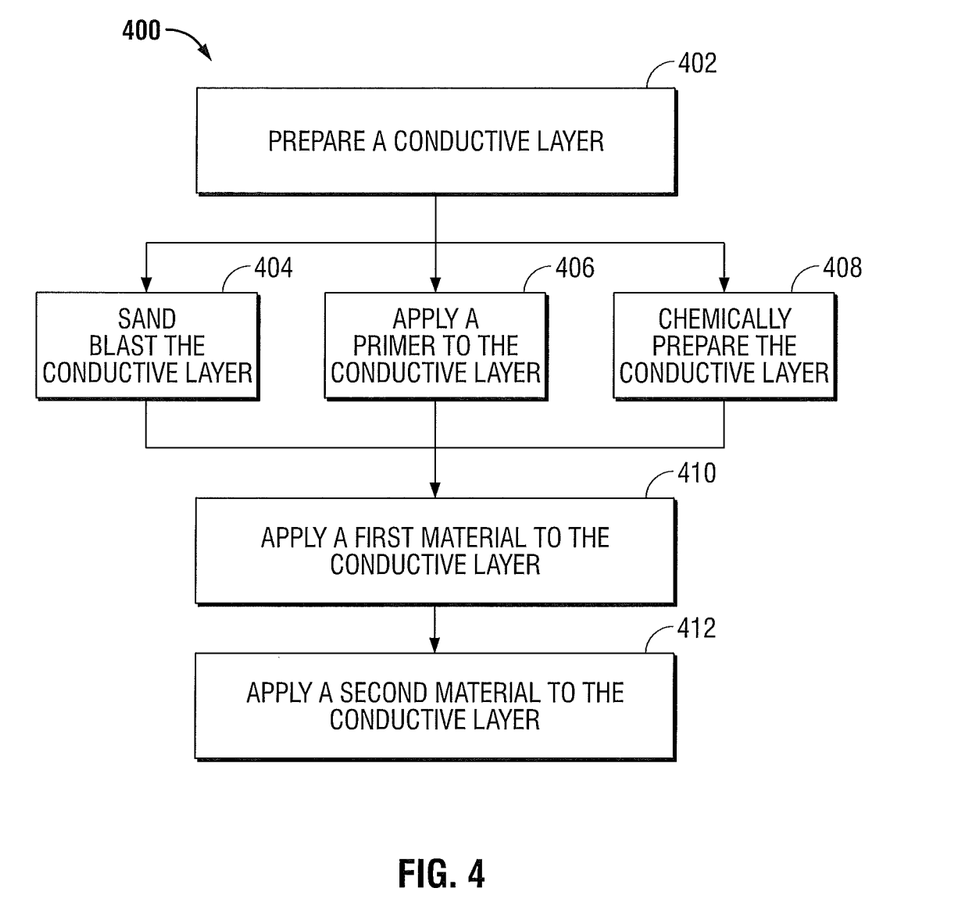
FIG. 4 is a flow chart illustrating a method for coating an electrode in accordance with an embodiment of the present disclosure.

FIG. 4 is a flow chart of a method 400 of coating an electrode of an electrosurgical instrument and includes steps 402-412. Step 402 prepares an electrode utilizing one or more of steps 404, 406, and 408. Step 404 sand or grit blasts the conductive layer 118. Step 406 applies a primer to the electrode, and step 408 chemically treats the conductive layer 118. Any number, either none or all, of the steps 402, 404, 406, and 408 may be performed depending on the materials being used. Step 410 applies the first material 120 to the conductive layer 118, and step 412 applies a second material to the electrode as described above. The preparation steps 404, 406, and/or 408, may facilitate adhesion of one or more of the subsequent material layers.

Steps 410 and 412 may use various techniques to apply the first and second materials. Specifically, Step 410 and/or 412 may use one or more of sputtering, flame spraying, spraying, dipping, vapor deposition, printing, and ionic deposition. Steps 410 and/or 412 may be controlled for porosity, masking pattern, and droplet size.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An electrosurgical instrument, comprising:
a substrate;
a conductive layer disposed on the substrate; and
a coating layer disposed on the conductive layer, the coating layer including:
a first layer including a first material, the first layer disposed at least partially over the conductive layer, the first layer including a plurality of surface features and a plurality of spaces therebetween, the plurality of surface features extending transversely with respect to a plane defined by the conductive layer; and a second layer including a second material that is insulative, flexible, and different from the first material, the second layer disposed at least partially over the first layer and covers at least a portion of the plurality of spaces, such that at least a portion of the plurality of surface features extend beyond the second layer, wherein the surface features are permanently fixed to the conductive layer and include ceramic and are arranged in a plurality of rows separated by a first distance and a plurality of columns separated by a second distance, the first material having a first dielectric constant of from 2.9 to 2,500, and the second material having a second dielectric constant of from 1.0 to 35.

2. The instrument according to claim 1, wherein the electrosurgical instrument is a monopolar electrosurgical instrument.

3. The instrument according to claim 1, wherein the electrosurgical instrument is a bipolar electrosurgical instrument.

4. The instrument according to claim 1, wherein at least one of the first material or the second material is porous.

5. The instrument according to claim 1, wherein the coating layer fully covers the conductive layer.

6. The instrument according to claim 1, wherein the first material and the second material are selected from the group consisting of a ceramic, a metal, a polymer, and combinations thereof.

7. The instrument according to claim 6, wherein the polymer is selected from the group consisting of polyethylene terephthalate, polytetrafluoroethylene, tetrafluoroethylene, poly(p-xylylene) and combinations thereof.

8. The instrument according to claim 6, wherein the ceramic is selected from the group consisting of zirconia, silica, porcelain, and combinations thereof.

9. The instrument according to claim 6, wherein the metal is selected from the group consisting of steel, copper, zinc, aluminum, brass, bronze, nickel, magnesium, titanium, and combinations thereof.

10. The instrument according to claim 1, wherein the first and second distances are the same.

11. The instrument according to claim 1, wherein the first and second distances are different.

12. The instrument according to claim 1, wherein at least a portion of the plurality of surface features at least partially extends through the second layer.

13. The instrument according to claim 1, wherein the first layer has a first portion disposed between and interconnecting a pair of adjacent surface features of the plurality of surface features, the first portion of the first layer in contact with and covering a first portion of the conductive layer.

14. The instrument according to claim 1, further comprising a support structure having a tissue-facing surface defining a cavity therein, wherein each of the substrate, the conductive layer, and the coating layer is received in the cavity.

15. The instrument according to claim 14, wherein the support structure is fabricated from an insulative material.

16. The electrosurgical instrument according to claim 1, wherein each of the plurality of surface features is at least one of conical, polygonal or frustoconical in shape.

17. An electrosurgical instrument, comprising:
a substrate;
a conductive layer disposed on the substrate; and
a coating layer disposed on the conductive layer, the coating layer including:
a first layer including a first material, the first layer disposed at least partially over the conductive layer, the first layer including a plurality of surface features and a plurality of spaces therebetween, the plurality of surface features extending perpendicularly with respect to a plane defined by the conductive layer; and
a second layer including a second material that is insulative, flexible, and different from the first material, the second layer disposed at least partially over the first layer and covers at least a portion of the plurality of spaces, such that at least a portion of the plurality of surface features extend beyond the second layer,
wherein the surface features are permanently fixed relative to the conductive layer and include ceramic and are arranged in a plurality of rows separated by a first distance and a plurality of columns separated by a second distance.

18. The electrosurgical instrument according to claim 17, wherein the second material has a dielectric constant from 0.14% to 700% of a dielectric constant of the first material.

* * * * *